United States Patent [19]
Hendrick

[11] Patent Number: 6,039,564
[45] Date of Patent: Mar. 21, 2000

[54] BUCCAL SHEATH AND IMPROVED ORTHODONTIC SYSTEM AND METHOD USING SAME

[76] Inventor: Paul P. Hendrick, 233 Tremont Park Dr. SE., Lenoir, N.C. 28645-4628

[21] Appl. No.: 09/287,220

[22] Filed: Apr. 5, 1999

[51] Int. Cl.[7] .................................................... A61C 3/00
[52] U.S. Cl. ............................................................ 433/17
[58] Field of Search ................................. 433/17, 5, 7, 20

[56] References Cited

U.S. PATENT DOCUMENTS

| | | | |
|---|---|---|---|
| 3,335,496 | 8/1967 | Andrews et al. | 433/17 |
| 4,037,324 | 7/1977 | Andreasen | 433/24 |
| 4,216,583 | 8/1980 | Reynolds | 433/17 |
| 4,490,112 | 12/1984 | Tanaka et al. | 433/20 |
| 4,498,867 | 2/1985 | Kesling | 433/17 |
| 4,818,226 | 4/1989 | Berendt et al. | 433/20 |
| 4,963,092 | 10/1990 | Snead | 433/17 |
| 5,007,828 | 4/1991 | Rosenberg | 433/17 |
| 5,017,133 | 5/1991 | Miura | 433/20 |
| 5,044,947 | 9/1991 | Sachdeva et al. | 433/20 |
| 5,102,333 | 4/1992 | Suzuki et al. | 433/24 |
| 5,288,229 | 2/1994 | Huff et al. | 433/17 |
| 5,312,247 | 5/1994 | Sachdeva et al. | 433/7 |
| 5,399,087 | 3/1995 | Arndt | 433/7 |
| 5,399,088 | 3/1995 | Mechley | 433/20 |
| 5,464,349 | 11/1995 | Andreiko et al. | 433/24 |
| 5,538,422 | 7/1996 | Arndt | 433/7 |
| 5,707,232 | 1/1998 | Strauss et al. | 433/17 |

*Primary Examiner*—John J. Wilson
*Attorney, Agent, or Firm*—Ohlandt, Greeley, Ruggiero & Perle, LLP; George W. Rauchfuss, Jr.

[57] ABSTRACT

A buccal sheath for conducting orthodontic procedures for alignment or movement of a patient's teeth permits anterior-posterior and/or lateral expansion of a palatial arch of the patient. The buccal sheath has a slot located in the body of the sheath, the slot running longitudinally, i.e., horizontally from an anterior end of the buccal sheath a portion of distance, generally about 80 to 90% of the distance, between the anterior and posterior end of the buccal sheath an adapted to receive and retain therein various archwires for either anterior-posterior movement, lateral (palatial) movement, or simultaneous movement in both the anterior-posterior direction or in lateral directions. The slot receives the archwires but prevents them from passing through the buccal sheath.

18 Claims, 3 Drawing Sheets

6,039,564

BUCCAL SHEATH AND IMPROVED ORTHODONTIC SYSTEM AND METHOD USING SAME

FIELD OF THE INVENTION

This invention relates to a buccal sheath and an orthodontic system and method for expanding the dental arch in four directions. More particularly this invention relates to a buccal sheath and the use thereof in an orthodontic system and method for expanding the dental arch in two or four directions.

BACKGROUND OF THE INVENTION

Orthodontic systems to move or adjust the orientation of malaligned teeth to their proper position or orientation generally involves attachment of brackets to individual teeth, generally by means of bands that encircle the teeth or by adhesion. To these brackets are connected orthodontic shape-recovery wires constructed and attached to create an orthodontic force to move or adjust the teeth to the desired position or orientation, Generally, this orthodontic procedure is quite complicated and often requires first repositioning of a patient's maxillary and mandibular first permanent molars or even removal of bicuspids or premolars. In order to reposition the maxillary first permanent molars, it is generally necessary to expand the palate, using various types of arch bars and lingual brackets to apply pressure against the lingual side of the molars. This repositioning procedure also generally requires reshaping the archwire and reinstallation of different wires over a significant period of time.

Then, generally after the molars have been repositioned to the proper location, appropriate brackets or buccal tubes are placed on the other individual teeth of the patient, the brackets having slots or channels therethrough for accepting and anchoring suitable orthodontic archwires to apply appropriate forces to the out-of-position teeth to urge them into proper position.

In the heretofore practice of these orthodontic methods, the distal end portions of the archwires are placed in and through the brackets or buccal tubes and the distal ends of the wire crimped, dimpled or bent to secure the archwire in the bracket or buccal tube. Such crimped, dimpled or bent distal ends of archwires are a hazard to the cheeks of the patient. Moreover, as the misplaced teeth begin to move, it becomes necessary to unsecure the archwire from the brackets and tubes and repeat the distal and securing procedure with new archwires. It is to be appreciated this orthodontic procedure described hereinbefore requires a significant amount of patient chair-time and numerous re-anchoring of archwires. Moreover, expansion of the palate and repositioning of the out-of-position teeth requires separate procedures and separate brackets. It is, therefore, highly desirable that an orthodontic method and system be provided which avoids these and other numerous drawbacks.

SUMMARY OF THE INVENTION

The invention provides a novel buccal sheath and a novel orthodontic system and method employing the buccal sheath that permits teeth movement in four directions without necessity for removal or changing of brackets or tubes and avoids the use of palatal archwires and lingual brackets or lingual sheaths and tubes. The invention also provides a novel orthodontic method and system for adjusting teeth in either of two directions, anterior-posterior or laterally, or in all four directions. The invention further provides an orthodontic method and system utilizing a novel buccal sheath whereby the necessity to crimp, dimple or bend distal ends of archwires is avoided as is all the inconvenience and additional orthodontic work associated therewith.

The invention also provides a novel orthodontic method or system whereby bicuspid or premolar extraction is generally avoided. The novel method and system with the novel buccal sheath also eliminates the need for headgear and lip bumbers generally associated with prior orthodontic procedures, and also avoids cheek irritation. Moreover, the need for patient cooperation is essentially eliminated with the novel orthodontic procedure and system of the invention. A significant advantage of the orthodontic system and method of the invention is that it enables the orthodontic practitioner to shorten treatment time by several months, generally by up to about six months.

The orthodontic method and system of the invention can be used with both adults and adolescents and also used to correct minor relapse mis-alignments of teeth that may occur such as due to loss of retainers.

The greatly improved orthodontic method and system of the invention is achieved by a novel buccal sheath which has an archwire-receiving slot in the sheath that extends only a portion of the longitudinal direction of the buccal sheath, as described in greater detail hereinafter.

DETAILED DESCRIPTION OF THE INVENTION

Figure 1:
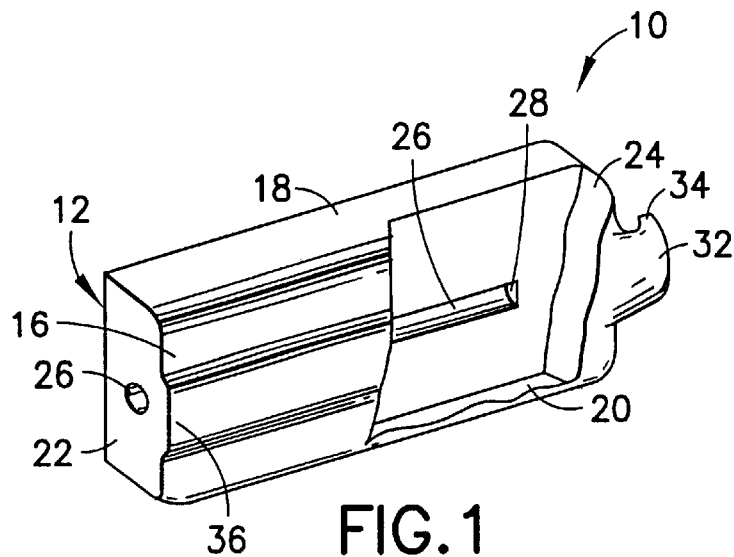
FIG. 1 is a front perspective view, partially cut away, of a buccal sheath of the invention.
Figure 2:
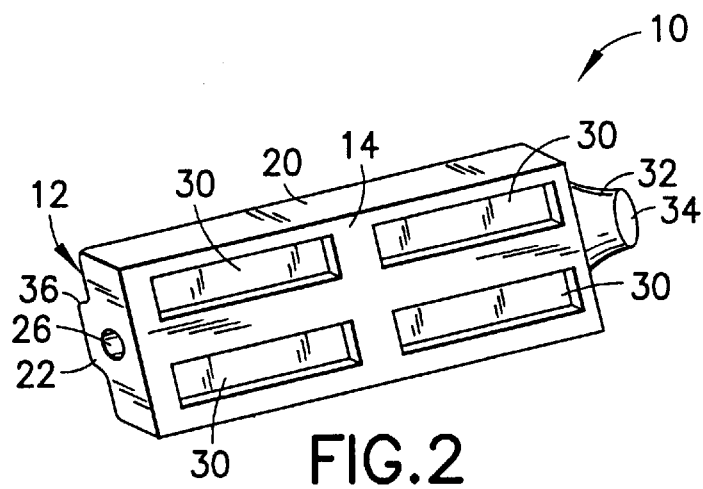
FIG. 2 is a rear perspective view of the buccal sheath of FIG. 1.

In FIGS. 1 and 2 there is illustrated a buccal sheath 10 of the present invention. Buccal sheath 10 comprises a body 12, generally rectangular or square in shape, although other shapes, even rounded shapes, are possible. The body 12 of the sheath is formed with a base surface 14 for attachment to the buccal side of a molar of a patient. Opposite the base surface 14 is a buccal base surface 16 separated from the base surface 16 on first opposite sides thereof by a horizontal gingival face surface 18 and a horizontal occlusal face surface 20 and on second opposite sides thereof by a vertical anterior end surface 22 and a vertical posterior end surface 24. Horizontal and vertical positions referring to positions with respect to the buccal sheath 10 when it is placed on a tooth of a patient.

Figure 5:
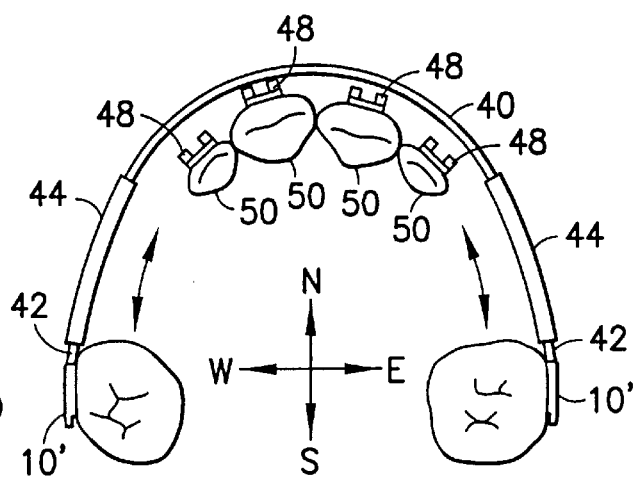
FIG. 5 is an occlusal view of an orthodontic system of this invention for adjusting the position of the maxillary teeth of a patient, shown prior to attachment of the archwire to the incisors of the patient.
Figure 6:
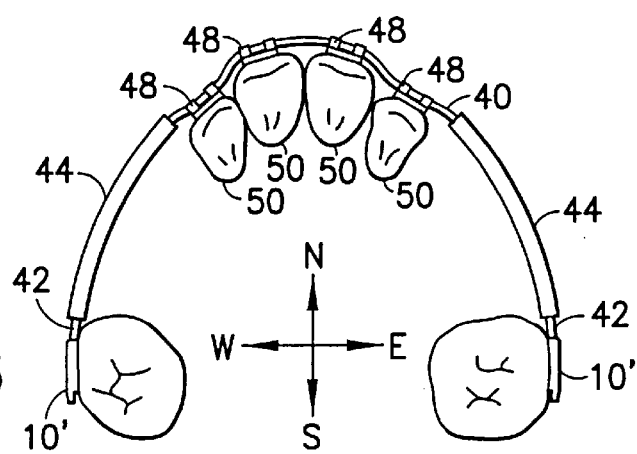
FIG. 6 is an occlusal view of a system of FIG. 5 with the archwire shown attached to the incisors of the patient.

Body 12 is provided with a generally medially placed horizontal slot 26 commencing at anterior end surface 22 and continuing longitudinally through the body for a distance to a position 28 where the slot terminates short of the posterior end surface 24. Slot 26 may extend any suitable longitudinal distance from the anterior end surface 22 to short of the posterior end surface 24, preferably about 80 to 90% of the longitudinal distance between the two end surfaces. Slot 26 is sized and adapted to receive a suitable orthodontic archwire as illustrated in FIGS. 4 to 6 as discussed hereinafter.

Figure 4:
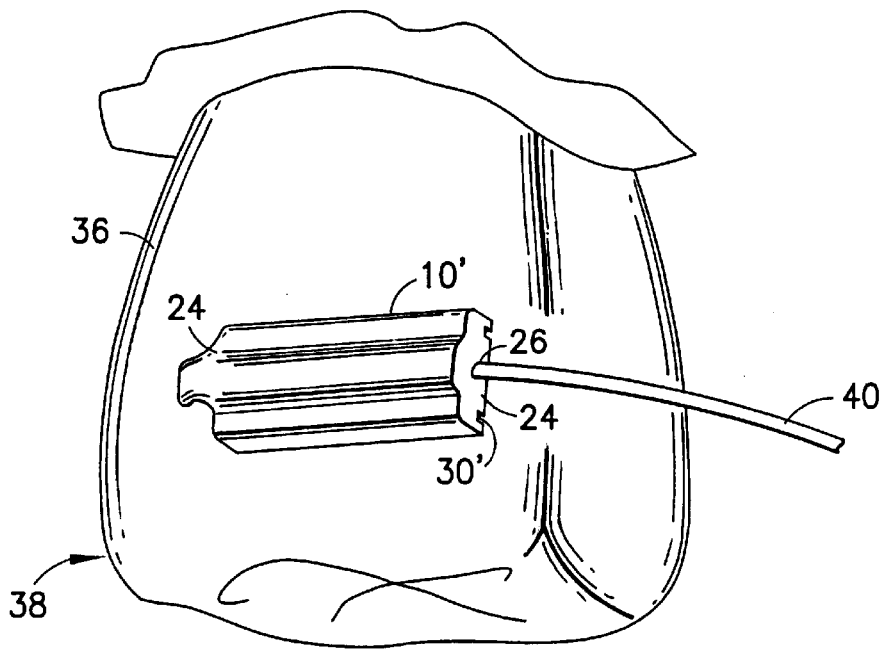
FIG. 4 is a perspective view of the buccal sheath of FIG. 3 attached to a molar of a patient.

Buccal sheath 10 is provided with one or more suitably shaped recesses 30 in base surface 14 for receiving adhesive material (not shown) to anchor the base surface of the buccal sheath to a buccal side of a molar of a patient as illustrated in FIG. 4. Alternatively, the sheath may be attached to molar bands placed on molars of a patient, such as by adhesively attaching or welding of the sheath to the molar bands.

The posterior end surface 24 of the buccal sheath 10 may, if desired, be provided with any suitable shaped protrusion 32 extending posteriority therefrom for receiving orthodontic elastics or springs used during an orthodontic procedure. Preferably, the protrusion 32 is generally an L- or hook-shaped protrusion with the hook portion 34 facing towards base surface 14, or if the buccal sheath is metal, the hook protrusion may face the gingivia.

It may also be desirable to provide the buccal face surface 16 of the buccal sheath with a medially spaced raised ridge surface 36 for minimizing contact of buccal sheath 10 with the cheek surface of a patient.

Figure 3:
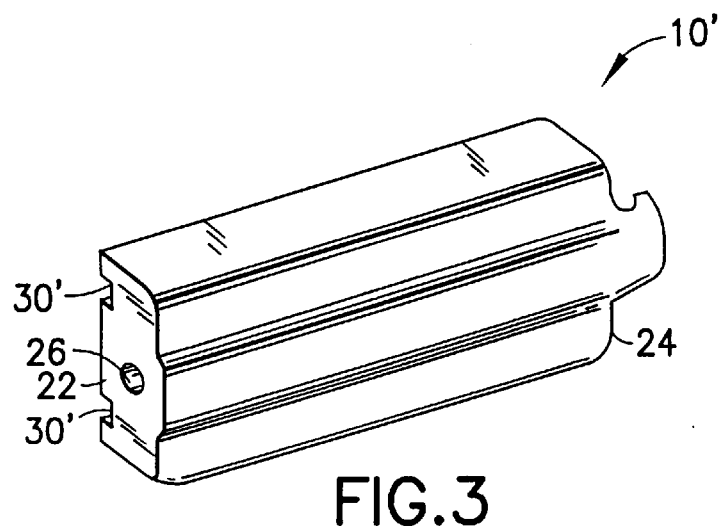
FIG. 3 is a front perspective view of another embodiment of a buccal sheath of the invention.

FIG. 3 illustrates a buccal sheath 10' similar to the buccal sheath illustrated in FIGS. 1 and 2 but with differently shaped recesses on the base surface. As illustrated in FIG. 3, the recesses may be in the form of one or more channels 30' extending along the length of the base surface.

If the buccal sheath is formed from metal, the base may be mesh and/or micro-etched, as described in connection with FIG. 7 to provide aperture recesses.

The buccal sheath 10 may be formed of any suitable material, such as for example, a thermoplastic, a plastic composite, a ceramic material, fiberglass, or metal or any other suitable material of choice, but is preferably formed as a molded thermoplastic or metal body.

Mounting and use of buccal sheaths of this invention is illustrated in FIGS. 4 to 6. In FIG. 4, buccal sheath 10' is illustrated as positioned and mounted on the buccal facing surface 36 of a molar 38 and positioned horizontally on the molar within a mouth such that the anterior end surface 22 is oriented toward the front of the mouth while the posterior end surface 24 is oriented toward the back or rear of the mouth. The buccal sheath is generally placed and anchored on the mesio-facial ⅓ of the first molar of a patient. Anchoring the buccal sheath on the tooth is preferably accomplished with a suitable adhesive in the recesses, such as, for example, by use of a UV light curable adhesive such as Transbond XT, available from 3M Unitek.

Once buccal sheaths 10' are suitably anchored on an maxillary and/or mandibular set of molars, a desired archwire 40 has its distal ends 42 and 44 (FIGS. 5 and 6) inserted into horizontal slots 26 of each buccal sheath 10' on a set of molars. The archwire employed is selected for the particular orthodontic adjustment desired for the teeth of a patient. Such archwires are known in the art. For example, to accomplish movement of the teeth in all four directions, namely both anterior-posterior (N ⇌S) and lateral (E ⇌W) expansion as illustrated in FIGS. 5 and 6, one may employ an oversized spooled straight 0.014 or 0.016 nickel-titanium wire sized so that its distal ends touch the ends 28 of both buccal sheath at the same time. For an orthodontic procedure requiring only lateral palatal expansion, a spooled straight 0.014 or 0.016 nickel-titanium wire that does not touch the closed ends 28 of the slots in both buccal sheath at the same time, or a straight Australian wire may be employed. For an orthodontic procedure only requiring anterior-posterior movement of the anterior teeth and/or molar distalization, one may use a preformed 0.014 or 0.016 nickel-titanium mandibular archwire. Optionally, if desired, suitable protective tubing 44 may be placed on the orthodontic wires in the area where the bicuspid area of the teeth are located.

As shown in FIGS. 5 and 6, suitable mounting bands or brackets 48, generally of stainless steel, and known in the art, are mounted to two or more, preferably to all four, incisor teeth 50. The archwire 40, which is an oversized spooled straight nickel-titanium wire for four directional movement of the teeth and has been sized to stand out in front of the central incisors a suitable distance, such as a distance of about 1.5 to 2 mm, is then tied-in or anchored to the central incisors and then the lateral incisor teeth so that there is then a slight bulge of about 1.5 to 2.0 mm in the archwire in the area between the incisors and the molars. These bulged areas will act to move the teeth and, over a period of time, the bulges will dissipate as movement of the teeth occurs. The archwire is then removed and replaced with a second archwire 2 mm longer than the removed archwire and the teeth movement process continues. This procedure is repeated by increasing the length and gauge of the archwire until the desired amount of expansion is achieved.

If movement of bicuspids is desired, brackets or bands can be mounted to the bicuspids and the archwire anchored to the brackets on the bicuspids.

If the incisors need to be intruded or extruded, then a preformed archwire may be employed after the initial alignment has been completed. For example, an 0.018 or 0.020 stainless steel archwire is bent, at about 30° in the direction desired to move the incisors, in front of the distal ends thereof and the wire is placed in the buccal sheaths.

Figure 7:
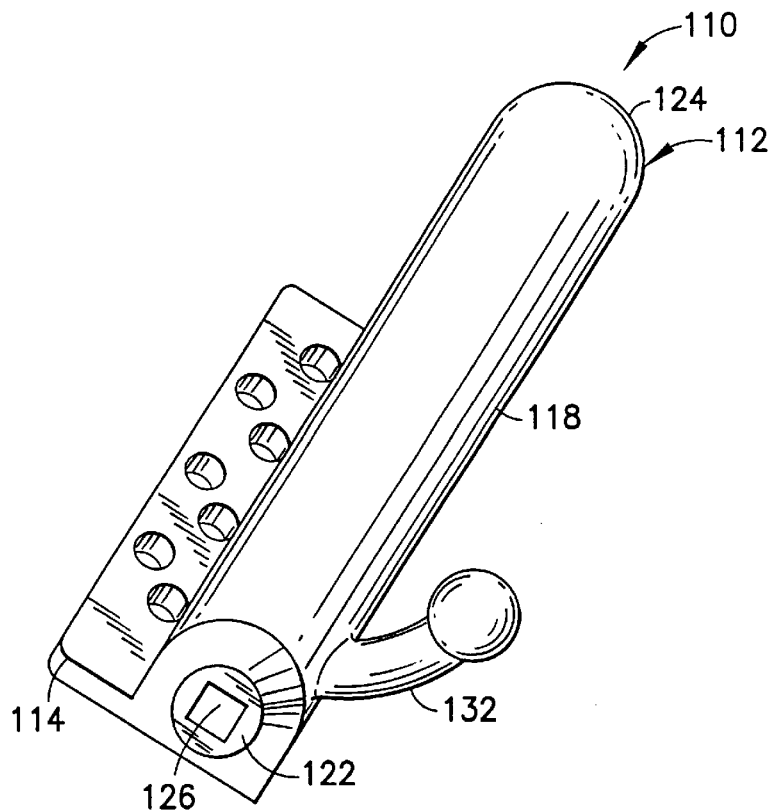
FIG. 7 is a perspective view of another embodiment of a buccal sheath of this invention.
Figure 8:
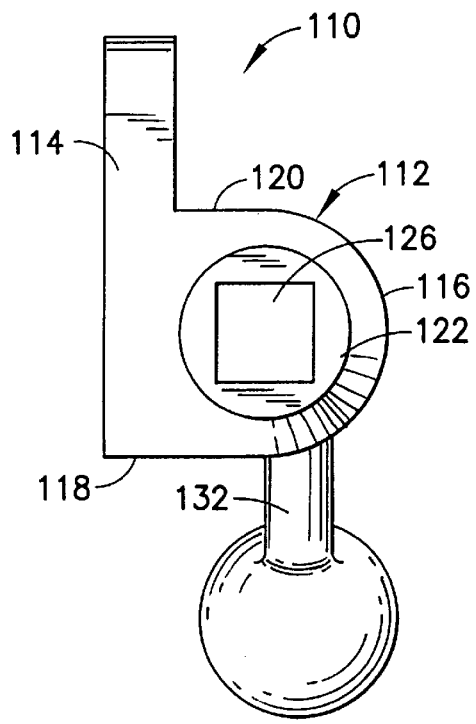
FIG. 8 is a side elevational view of the buccal sheath of FIG. 7.

Another embodiment of a buccal sheath of the invention is shown in FIGS. 7 and 8. The buccal sheath 110 is preferably a metal sheath. Buccal sheath 110 comprises a body 112 of any suitable shape, generally a rectangular shape with rounded edges. The body 112 is formed with a base surface 114 for attachment to the buccal side of a molar, either directly to the molar or by attachment to molar bands on the molar of a patient. The body 112 provides buccal face surface 116, horizontal gingival face surface 118 and horizontal occlusal face surface 120. Body 112 is provided with a generally medially placed horizontal slot 126 commencing at anterior end surface 122 and continuing longitudinally through the body to a position where the slot terminates short of the posterior end surface 124 of the body. Generally, slot 126 will extend about 80% to 90% of the longitudinal distance between anterior end 124 and posterior end 126. Buccal sheath 110 is provided with a plurality of apertures 130 for use in attaching the sheath to a molar or molar bands on a molar of a patient. Apertures 130 may be provided by the metal of base surface 114 being a mesh surface or the apertures may, for example, be micro-etched into the metal of the base surface. Buccal sheath 110 may also be provided with a suitably shaped protrusion 132 extending posteriority or gingivally from body 112 receiving Class 11 or 111 elastics or chain elastics.

With the novel buccal sheaths of this invention, one can obtain expansion of the dental arch in all four directions at once, or only laterally, or only in an anterior-posterior expansion depending upon the choice of archwire employed.

Upon completion of the expansion process the archwire or archwires is/are removed, as are the bands on the incisors and the buccal sheath on the molars. The buccal sheaths of this invention are easily removed such as by prying them with a scaler, preferably by prying the hook portion 34 with a scaler.

In addition to the buccal sheath of the invention providing means for obtaining expansion of a patient's teeth in all four directions or in only two directions, the buccal sheaths are easy to use and patient friendly and reduces and essentially eliminates the need for patient cooperation in the teeth movement portion of the orthodontic procedure. Furthermore, the buccal sheaths of this invention enables a practitioner to employ the sheaths and orthodontic procedure without crimps, dimples, bends or the like being required in protruding distal ends of archwires. Moreover, there is no need for wax to protect the patient's cheek from the distal ends of the archwire nor is there a requirement for headgear, lip bumpers or molar distalizers. Additionally, the buccal sheath generally enables the orthodontic procedure to be accomplished without the need for bicuspid extractions or cross palate archwires.

It will be apparent from the foregoing objects and description of illustrative embodiments of the invention that various modifications can be made in the construction and operation of the buccal sheath orthodontic method of this invention without departing from the spirit and scope of the invention and it is intended that the foregoing descriptive is illustrative and not limiting of the embodiment of the invention.

I claim:

1. An orthodontic appliance for attachment to the buccal side of a molar of a patient in need of alignment or movement of teeth of the patient, the orthodontic appliance comprising a buccal sheath, said buccal sheath comprising:
    a body member having a base surface for fixedly attaching to the buccal side of a molar of the patient and a generally medially spaced slot in the body member, the slot commencing at an anterior end surface of the body and continuing a longitudinal distance through the body member and terminating in a position short of an opposite posterior end surface of the body for receiving and retaining an orthodontic wire member for permitting anterior-posterior movement of teeth and/or lateral expansion of the palatal arch of the patient.

2. The buccal sheath of claim 1, wherein the longitudinal distance the slot extends in the body is about 80% of the distance between the anterior and posterior end surfaces.

3. The buccal sheath of claim 1, wherein said base surface comprises a plurality of recesses or apertures for receiving adhesive material to anchor the base surface to a buccal side of a molar of a patient.

4. The buccal sheath of claim 3, wherein the posterior end surface has a protrusion extending therefrom for receipt of orthodontic elastics or springs.

5. A method of orthodontic treatment of the mandibular and/or maxillary teeth of a person in need thereof, said method comprising:
    fixedly attaching a buccal sheath according to claim 1 to each of the two first molars of mandibular and/or maxillary teeth of the person,
    bracketing at least two incisors of the mandibular and/or maxillary teeth of the person with brackets for receiving an orthodontic wire,
    inserting a terminal end of an orthodontic wire in the slot of each buccal sheath on each of the two first molars and attaching the orthodontic wire in the brackets on the incisors,
    permitting the orthodontic wire to produce anterior-posterior and/or lateral movement of the person's teeth over a period of time.

6. The method according to claim 5, wherein the orthodontic wire is a preformed archwire for producing anterior-posterior movement of teeth of the person.

7. The method according to claim 5, wherein the orthodontic wire is a spooled straight wire for producing lateral movement of teeth of the person.

8. The method according to claim 5, wherein the orthodontic wire is an oversized spooled wire for producing both anterior-posterior and lateral movement of teeth of the person.

9. An orthodontic appliance comprising a buccal sheath for attachment to a molar for use in alignment or movement of teeth of a patient in need thereof, said buccal sheath comprising:
    a body having a base surface for fixedly attaching to a buccal side of a molar of said patient, a gingival face surface and an occlusal face surface with each being adjacent the base surface, a buccal face surface intermediate the gingival and occlusal face surfaces, an anterior end surface and a posterior end surface generally transverse to the base, occlusal, gingival and buccal face surfaces, a generally medially spaced slot in the body member, said slot commencing at the anterior end surface, continuing a longitudinal distance through the body member and terminating at a position short of the posterior end surface for receiving and retaining an orthodontic wire member for permitting anterior-posterior movement of teeth and/or lateral expansion of a palatal arch of a patient.

10. An orthodontic appliance according to claim 9 wherein:
    the gingival face surface is adjacent a first side of the base surface and the occlusal face surface is adjacent a second side of the base surface and opposite the first side.

11. A method of orthodontic treatment of the mandibular and/or maxillary teeth of a person in need thereof, said method comprising:
    fixedly attaching a buccal sheath according to claim 10 to each of the two first molars of mandibular and/or maxillary teeth of the person,
    bracketing at least two incisors of the mandibular and/or maxillary teeth of the person with brackets for receiving an orthodontic wire,
    inserting a terminal end of an orthodontic wire in the slot of each buccal sheath on each of the two first molars and attaching the orthodontic wire in the brackets on the incisors,
    permitting the orthodontic wire to produce anterior-posterior and/or lateral movement of the person's teeth over a period of time.

12. The method according to claim 11, wherein the orthodontic wire is a preformed archwire for producing anterior-posterior movement of teeth of the person.

13. The method according to claim 11, wherein the orthodontic wire is a spooled straight wire for producing lateral movement of teeth of the person.

14. The method according to claim 11, wherein the orthodontic wire is an oversized spooled wire for producing both anterior-posterior and lateral movement of teeth of the person.

15. A method of orthodontic treatment of the mandibular and/or maxillary teeth of a person in need thereof, said method comprising:

fixedly attaching a buccal sheath according to claim 9 to each of the two first molars of mandibular and/or maxillary teeth of the person, bracketing at least two incisors of the mandibular and/or maxillary teeth of the person with brackets for receiving an orthodontic wire, inserting a terminal end of an orthodontic wire in the slot of each buccal sheath on each of the two first molars and attaching the orthodontic wire in the brackets on the incisors, permitting the orthodontic wire to produce anterior-posterior and/or lateral movement of the person's teeth over a period of time.

16. The method according to claim 15, wherein the orthodontic wire is a preformed archwire for producing anterior-posterior movement of teeth of the person.

17. The method according to claim 15, wherein the orthodontic wire is a spooled straight wire for producing lateral movement of teeth of the person.

18. The method according to claim 15, wherein the orthodontic wire is an oversized spooled wire for producing both anterior-posterior and lateral movement of teeth of the person.

* * * * *

UNITED STATES PATENT AND TRADEMARK OFFICE
CERTIFICATE OF CORRECTION

PATENT NO. : 6,039,564
DATED : March 21, 2000
INVENTOR(S) : Paul P. Hedrick

It is certified that error appears in the above-identified patent and that said Letters Patent is hereby corrected as shown below:

On the title page, item [76], the Inventor's name should read ---Paul P. Hedrick---.

Signed and Sealed this

Thirteenth Day of March, 2001

Attest:

NICHOLAS P. GODICI

*Attesting Officer*   *Acting Director of the United States Patent and Trademark Office*